United States Patent
Tunheim et al.

(10) Patent No.: US 9,395,294 B2
(45) Date of Patent: Jul. 19, 2016

(54) SYSTEMS AND METHODS FOR MONITORING CHEMICAL PROCESSES

(71) Applicant: Halliburton Energy Services, Inc., Houston, TX (US)

(72) Inventors: Ola Tunheim, Bryne Rogaland (NO); Robert P. Freese, Pittsboro, NC (US); Alexis Wachtel, Houston, TX (US); James Robert MacLennan, Aberdeen Grampian (GB)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/726,806

(22) Filed: Jun. 1, 2015

(65) Prior Publication Data

US 2015/0293013 A1 Oct. 15, 2015

Related U.S. Application Data

(62) Division of application No. 13/615,882, filed on Sep. 14, 2012, now Pat. No. 9,086,383.

(51) Int. Cl.
*G01N 21/00* (2006.01)
*G01N 21/27* (2006.01)
*G01N 21/75* (2006.01)
*G01N 21/31* (2006.01)

(52) U.S. Cl.
CPC .............. *G01N 21/272* (2013.01); *G01N 21/75* (2013.01); *G01N 21/31* (2013.01); *G01N 2021/755* (2013.01); *G01N 2021/757* (2013.01); *G01N 2201/06* (2013.01)

(58) Field of Classification Search
CPC .......................... G01N 21/6486; G01N 21/65
USPC ........................................ 436/164, 170, 171
See application file for complete search history.

(56) References Cited

U.S. PATENT DOCUMENTS

| 9,086,383 | B2 | 7/2015 | Tunheim et al. | |
| 2002/0154315 | A1* | 10/2002 | Myrick | G01J 3/18 356/305 |
| 2006/0142955 | A1 | 6/2006 | Jones et al. | |
| 2008/0133193 | A1 | 6/2008 | Gdanski et al. | |
| 2009/0188665 | A1 | 7/2009 | Tubel et al. | |
| 2010/0195105 | A1 | 8/2010 | Myrick et al. | |
| 2010/0265509 | A1 | 10/2010 | Jones et al. | |
| 2012/0162638 | A1 | 6/2012 | Villeneuve | |

OTHER PUBLICATIONS

Official Action for Singapore Patent Application No. 11201500781Q dated Jul. 3, 2015.
Official Action for New Zealand Patent Application No. 704677 dated Jul. 8, 2015.

* cited by examiner

*Primary Examiner* — Natalia Levkovich
(74) *Attorney, Agent, or Firm* — McDermott Will & Emery LLP; Alan Bryson

(57) ABSTRACT

A method of monitoring a fluid includes containing the fluid within a flow path, the fluid having a chemical reaction occurring therein. At least one integrated computational element is optically interacted with the fluid, thereby generating optically interacted light. An output signal is then produced based on the optically interacted light that corresponds to a characteristic of the chemical reaction.

10 Claims, 2 Drawing Sheets

SYSTEMS AND METHODS FOR MONITORING CHEMICAL PROCESSES

BACKGROUND

The present invention relates to optical analysis systems and methods for analyzing fluids and, in particular, to systems and methods for monitoring chemical reaction processes in or near real-time.

In the oil and gas industry, it is often important to precisely know the characteristics and chemical composition of fluids as they circulate into and out of subterranean formations, vessels, and pipelines. Typically, oil and gas fluid analyses have been conducted off-line using laboratory analyses, such as spectroscopic and/or wet chemical methods, which analyze an extracted sample of the fluid. Depending on the analysis required, however, such an approach can take hours to days to complete, and even in the best case scenario, a job will often be completed prior to the analysis being obtained. Furthermore, off-line laboratory analyses can sometimes be difficult to perform, require extensive sample preparation and present hazards to personnel performing the analyses. Bacterial analyses, for example, can particularly take a long time to complete since culturing of a bacterial sample is usually needed to obtain satisfactory results.

Although off-line, retrospective analyses can be satisfactory in certain cases, but they do not provide real-time or near real-time analysis capabilities. As a result, proactive control of a subterranean operation or fluid flow within related vessels or pipelines cannot take place, at least without significant process disruption occurring while awaiting the results of the analysis. Off-line, retrospective analyses can also be unsatisfactory for determining true characteristics of a fluid since the characteristics of the extracted sample of the fluid oftentimes change during the lag time between collection and analysis, thereby making the properties of the sample non-indicative of the true chemical composition or characteristic. For example, factors that can alter the characteristics of a fluid during the lag time between collection and analysis can include, scaling, reaction of various components in the fluid with one another, reaction of various components in the fluid with components of the surrounding environment, simple chemical degradation, and bacterial growth.

Monitoring fluids in or near real-time can be of considerable interest in order to monitor chemical reaction processes, thereby serving as a quality control measure for processes in which fluids are used. Specifically, there are many chemical processes which require physical and chemical parameters to be altered based on the concentration of reactants in the process or products produced by the process. For example, temperatures, pressures, flow rates, pH and other physical parameters of the process must frequently be monitored and changed to optimize the progress of the chemical process.

Spectroscopic techniques for measuring chemical reaction processes are well known and are routinely used under laboratory conditions. In some cases, these spectroscopic techniques can be carried out without using an involved sample preparation. It is more common, however, to carry out various sample preparation procedures before conducting the analysis. Reasons for conducting sample preparation procedures can include, for example, removing interfering background materials from the analyte of interest, converting the analyte of interest into a chemical form that can be better detected by a chosen spectroscopic technique, and adding standards to improve the accuracy of quantitative measurements. Thus, there is usually a delay in obtaining an analysis due to sample preparation time, even discounting the transit time of transporting the extracted sample to a laboratory.

Although spectroscopic techniques can, at least in principle, be conducted at a job site, such as a well site, or in a process, the foregoing concerns regarding sample preparation times may still apply. Furthermore, the transitioning of spectroscopic instruments from a laboratory into a field or process environment can be expensive and complex. Reasons for these issues can include, for example, the need to overcome inconsistent temperature, humidity, and vibration encountered during field use. Furthermore, sample preparation, when required, can be difficult under field analysis conditions. The difficulty of performing sample preparation in the field can be especially problematic in the presence of interfering materials, which can further complicate conventional spectroscopic analyses. Quantitative spectroscopic measurements can be particularly challenging in both field and laboratory settings due to the need for precision and accuracy in sample preparation and spectral interpretation.

SUMMARY OF THE INVENTION

The present invention relates to optical analysis systems and methods for analyzing fluids and, in particular, to systems and methods for monitoring chemical reaction processes in or near real-time.

In some aspects of the disclosure, a system is disclosed that may include a flow path containing a fluid in which a chemical reaction is occurring, at least one integrated computational element configured to optically interact with the fluid and thereby generate optically interacted light, and at least one detector arranged to receive the optically interacted light and generate an output signal corresponding to a characteristic of the chemical reaction.

In other aspects of the disclosure, a method of monitoring a fluid is disclosed. The method may include containing the fluid within a flow path, the fluid having a chemical reaction occurring therein, optically interacting at least one integrated computational element with the fluid, thereby generating optically interacted light, and producing an output signal based on the optically interacted light that corresponds to a characteristic of the chemical reaction.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
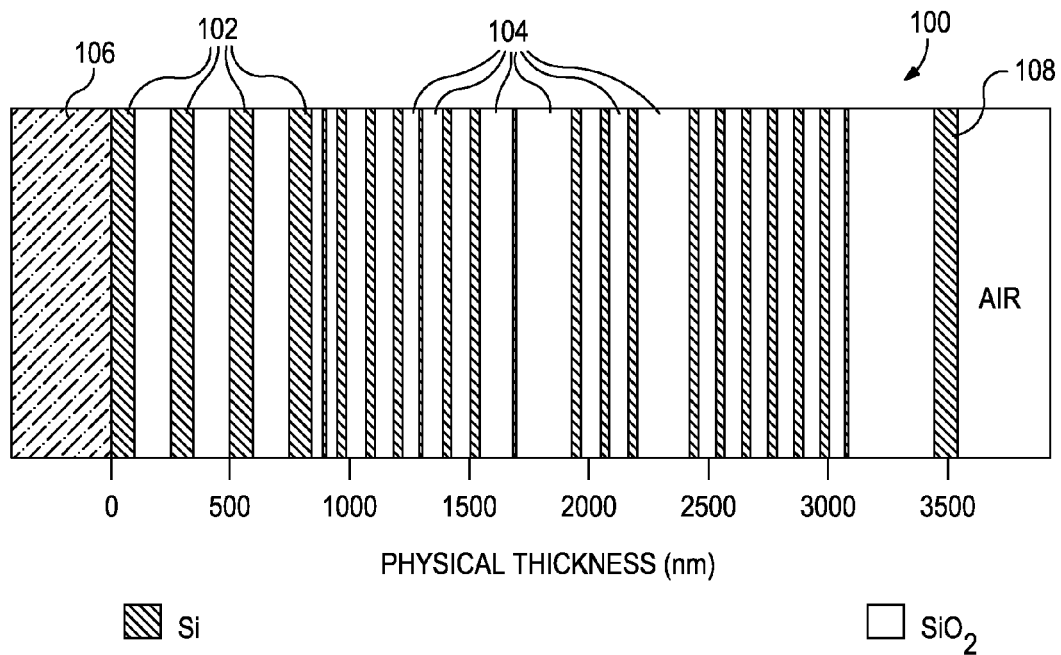
FIG. 1 illustrates an exemplary integrated computation element, according to one or more embodiments.

The present invention relates to optical analysis systems and methods for analyzing fluids and, in particular, to systems and methods for monitoring chemical reaction processes in or near real-time.

The exemplary systems and methods described herein employ various configurations of optical computing devices, also commonly referred to as "opticoanalytical devices," for the real-time or near real-time monitoring of chemical reaction processes. In operation, the exemplary systems and methods may be useful and otherwise advantageous in determining when a chemical reaction has proceeded to completion. In other embodiments, the systems and methods may provide a real-time or near real-time determination of the concentration of unreacted reagents and/or resultant products, thereby allowing chemical reaction kinetics to be determined. The optical computing devices, which are described in more detail below, can advantageously provide real-time or near real-time monitoring of a chemical reaction that cannot presently be achieved with either onsite analyses at a job site or via more detailed analyses that take place in a laboratory. A significant and distinct advantage of these devices is that they can be configured to specifically detect and/or measure a particular component or characteristic of interest of a fluid or other material, thereby allowing qualitative and/or quantitative analyses of the fluid to occur without having to extract a sample and undertake time-consuming analyses at an off-site laboratory. With the ability to undertake real-time or near real-time analyses, the exemplary systems and methods described herein may be able to provide some measure of proactive or responsive control over the chemical reaction, enable the collection and archival of fluid information in conjunction with operational information to optimize subsequent operations, and/or enhance the capacity for remote job execution.

Those skilled in the art will readily appreciate that the systems and methods disclosed herein may be suitable for use in the oil and gas industry since the described optical computing devices provide a cost-effective, rugged, and accurate means for monitoring chemical reactions related to hydrocarbon quality in order to facilitate the efficient management of oil/gas production. It will be further appreciated, however, that the various disclosed systems and methods are equally applicable to other technology or industry fields including, but not limited to, the chemicals industry, the food and beverage industries, the drug industry, the energy industry (e.g., manufacture and development of biofuels), industrial applications, mining industries, defense and military technologies, or any field where it may be advantageous to determine in real-time or near real-time the reaction kinetics of a chemical process.

The optical computing devices suitable for use in the present embodiments can be deployed at any number of various points within a flow path to monitor a chemical reaction occurring within a fluid or material. Depending on the location of the particular optical computing device, various types of information about the fluid or material can be obtained. In some cases, for example, the optical computing devices can be used to monitor a chemical reaction in real-time as a result of adding a treatment reagent to a fluid, removing a treatment reagent therefrom, or exposing the fluid or substance to a condition that potentially changes a characteristic of the fluid or substance in some way. In other cases, the optical computing devices can be used to determine the concentration of unreacted reagents of a chemical composition and any resulting products derived therefrom. This may prove advantageous in determining when the reaction has progressed to completion. Thus, the systems and methods described herein may be configured to monitor a fluid and, more particularly, to monitor chemical reaction processes related thereto.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid as found in the oil and gas industry. Fluids can include various flowable mixtures of solids, liquids and/or gases. Illustrative gases that can be considered fluids according to the present embodiments include, for example, air, nitrogen, carbon dioxide, argon, helium, methane, ethane, butane, and other hydrocarbon gases, combinations thereof and/or the like.

As used herein, the term "characteristic" refers to a chemical, mechanical, or physical property of a substance, such as the fluid defined above or a reagent as defined below. The characteristic may further refer to a chemical, mechanical, or physical property of a product resulting from a chemical reaction transpiring within the fluid. A characteristic of a substance may include a quantitative value of one or more chemical components therein. Such chemical components may be referred to herein as "analytes." Illustrative characteristics of a substance that can be monitored with the optical computing devices disclosed herein can include, for example, chemical composition (e.g., identity and concentration in total or of individual components), impurity content, pH, temperature, viscosity, density, ionic strength, total dissolved solids, salt content, porosity, opacity, bacteria content, combinations thereof, and the like. Moreover, the phrase "characteristic of interest of/in a fluid" may be used herein to refer to the characteristic of a chemical reaction transpiring or otherwise occurring therein.

As used herein, the term "flow path" refers to a route through which a fluid is capable of being transported between two or more points. In some cases, the flow path need not be continuous or otherwise contiguous between the two or more points. Exemplary flow paths include, but are not limited to, a flowline, a pipeline, a hose, a process facility, a storage vessel, a tanker, a railway tank car, a transport barge or ship, a separator, a contactor, a process vessel, combinations thereof, or the like. In cases where the flow path is a pipeline, or the like, the pipeline may be a pre-commissioned pipeline or an operational pipeline. It should be noted that the term "flow path" does not necessarily imply that a fluid is flowing therein, rather that a fluid is capable of being transported or otherwise flowable therethrough.

As used herein, the term "chemical reaction process" or "chemical reaction" refers to a process that leads to the transformation of one set of chemical substances to another. As known to those skilled in the art, chemical reactions involve one or more reagents, as described below, that chemically react either spontaneously, requiring no input of energy, or non-spontaneously typically following the input of some type of energy, such as heat, light, electricity, or through the addition of a catalyst. The chemical reaction process yields one or more products, which may or may not have properties different from the reagents. Some exemplary products that may be monitored or otherwise detected, as disclosed herein, include tetrakis hydroxymethyl phosphonium oxide (THPO), quaternary pyridinium compounds and the like, sulfites, sulfates, derivatives thereof, or the like.

As used herein, the term "reagent," or variations thereof, refers to at least a portion of a substance or material of interest to be evaluated using the optical computing devices described herein during a chemical reaction process. A reagent may be a reaction material that is transformed into a product during a particular chemical reaction. In some embodiments, the reagent is the characteristic of interest, as defined above, and may include any integral component of the fluid flowing within the flow path. For example, the reagent may include compounds containing elements including, but not limited to, barium, calcium, manganese, sulfur, iron, strontium, chlorine, and any other chemical substance that can lead to precipitation within a flow path. The reagent may also refer to paraffins, waxes, asphaltenes, aromatics, saturates, foams, salts, particulates, sand or other solid particles, combinations thereof, and the like.

In other aspects, the reagent may include any substance added to the flow path in order to cause a chemical reaction configured to treat the flow path or the fluid contained therein. Exemplary treatment reagents may include, but are not limited to, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers (e.g., $H_2S$ scavengers, $CO_2$ scavengers or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, tetrakis hydroxymethyl phosphonium sulfate (THPS), glutaraldehyde, benzalkonium chloride, algal/fungal/bacterial deposits, imidazoline derivatives, quaternary ammonium salts, alkaline zinc carbonate, amines, and the like. Combinations of these reagents can be used as well.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a fluid, or a reagent within the fluid, and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the fluid, such as a characteristic of a chemical process of interest transpiring in the fluid. The output of electromagnetic radiation from the processing element can be reflected electromagnetic radiation, transmitted electromagnetic radiation, and/or dispersed electromagnetic radiation. Whether reflected, transmitted, or dispersed electromagnetic radiation is eventually analyzed by the detector may be dictated by the structural parameters of the optical computing device as well as other considerations known to those skilled in the art. In addition, emission and/or scattering of the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a fluid or a reagent within the fluid.

The exemplary systems and methods described herein will include at least one optical computing device arranged along or in a flow path in order to monitor a fluid flowing or otherwise contained within the flow path. The at least one optical computing device may also be configured to monitor one or more reagents flowing or otherwise contained within the flow path, and any resulting products derived from chemical processes transpiring in the flow path. Each optical computing device may include an electromagnetic radiation source, at least one processing element (e.g., integrated computational element), and at least one detector arranged to receive optically interacted light from the at least one processing element. As disclosed below, however, in at least one embodiment, the electromagnetic radiation source may be omitted and instead the electromagnetic radiation may be derived from the fluid, the reagent, or the product itself. In some embodiments, the exemplary optical computing devices may be specifically configured for detecting, analyzing, and quantitatively measuring a particular characteristic or analyte of interest of the fluid, reagent, or product in the flow path. In at least one embodiment, the characteristic may be related to a chemical process of interest and the optical computing devices may be configured to numerically follow the reaction progress in near or real-time, thereby allowing reaction kinetics to be determined. In other embodiments, the optical computing devices may be general purpose optical devices, with post-acquisition processing (e.g., through computer means) being used to specifically detect the characteristic of the fluid or reagent.

In some embodiments, suitable structural components for the exemplary optical computing devices are described in commonly owned U.S. Pat. Nos. 6,198,531; 6,529,276; 7,123,844; 7,834,999; 7,911,605, 7,920,258, and 8,049,881, each of which is incorporated herein by reference in its entirety, and U.S. patent application Ser. Nos. 12/094,460; 12/094,465; and 13/456,467, each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments or uses disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics and/or analytes of interest of a fluid, including any reagents and/or products corresponding to a chemical reaction process that transpires therein. As a result, interfering signals are discriminated from those of interest in the fluid by appropriate configuration of the optical computing devices, such that the optical computing devices provide a rapid response regarding the characteristics of the fluid, reagent, and/or resulting product as based on the detected output. In some embodiments, the detected output can be converted into a voltage that is distinctive of the magnitude of the characteristic of interest being measured. The foregoing advantages and others make the optical computing devices particularly well suited for field and downhole use, but may equally be applied to several other technologies or industries, without departing from the scope of the disclosure.

The optical computing devices can be configured to detect not only the composition and concentrations of a reagent, or a product resulting from a chemical process involving the reagent, in a fluid, but they also can be configured to determine physical properties and other characteristics of the reagent and/or product as well, based on their analysis of the electromagnetic radiation received from the particular reagent/product. For example, the optical computing devices can be configured to determine the concentration of an analyte and correlate the determined concentration to a characteristic of a reagent or product by using suitable processing means. As will be appreciated, the optical computing devices may be configured to detect as many characteristic or analytes of the fluid, reagents, and/or products as desired. All that is required to accomplish the monitoring of multiple characteristics is the incorporation of suitable processing and detection means within the optical computing device for each analyte of interest, whether pertaining to the fluid, the reagent, and/or the product. In some embodiments, the properties of the fluid, reagent, and/or product can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given fluid, reagent, and/or product will be determined.

The optical computing devices described herein utilize electromagnetic radiation to perform calculations, as opposed to the hardwired circuits of conventional electronic processors. When electromagnetic radiation interacts with a fluid, or a reagent or product present within the fluid, unique physical and chemical information about the substance may be encoded in the electromagnetic radiation that is reflected from, transmitted through, or radiated therefrom. This information is often referred to as the spectral "fingerprint" of the substance. The optical computing devices described herein are capable of extracting the information of the spectral fingerprint of multiple characteristics or analytes within a fluid, reagent, and/or product, and converting that information into a detectable output regarding the overall properties of the monitored substance. That is, through suitable configurations of the optical computing devices, electromagnetic radiation associated with characteristics or analytes of interest in a fluid, reagent, and/or product can be separated from electromagnetic radiation associated with all other components of the fluid in order to estimate the properties of the monitored substance in real-time or near real-time.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a fluid. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest (e.g., a characteristic of a fluid, a reagent, or a product resulting from a chemical reaction) using a conventional spectroscopic instrument. The spectrum of interest of a given characteristic of interest typically includes any number of different wavelengths. It should be understood that the exemplary ICE 100 in FIG. 1 does not in fact represent any particular characteristic of interest of a given fluid, reagent, and/or product, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the materials to the monitored substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

Further information regarding the structures and design of exemplary integrated computational elements (also referred to as multivariate optical elements) is provided in Applied Optics, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2:
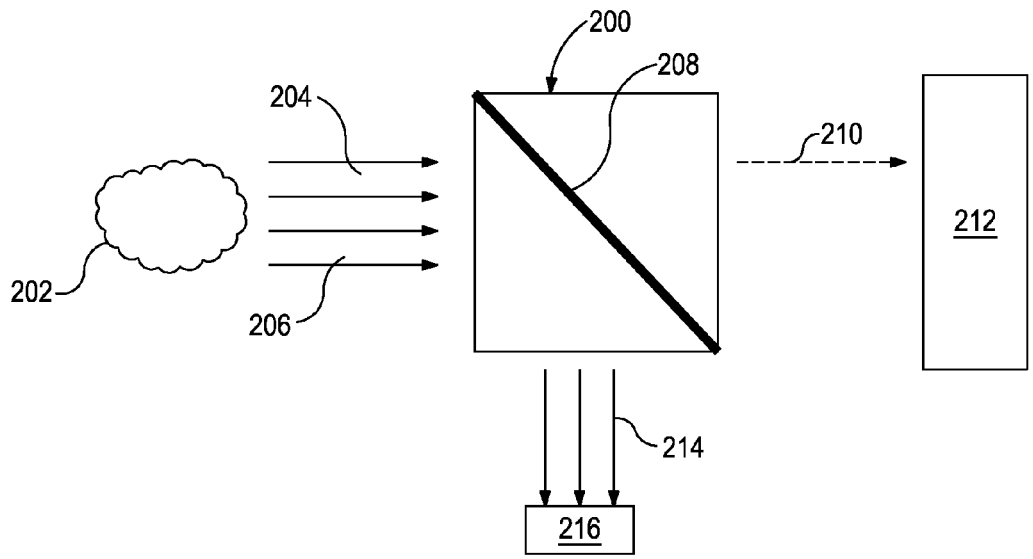
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of interest from other electromagnetic radiation. As shown in FIG. 2, after being illuminated with incident electromagnetic radiation, a fluid 202 containing a reagent (e.g., a characteristic of interest) produces an output of electromagnetic radiation (e.g., sample-interacted light), some of which is electromagnetic radiation 204 corresponding to the characteristic of interest and some of which is background electromagnetic radiation 310 corresponding to other components or characteristics of the fluid 202. In some embodiments, the fluid 202 may include one or more reagents and the characteristic of interest may correspond to the one or more reagents. In other embodiments, the fluid may include one or more products resulting from a chemical reaction occurring in the fluid and the characteristic of interest may correspond to the products.

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after a light source, which provides the initial electromagnetic radiation. Various configurations and applications of spectral elements in optical computing devices may be found in commonly owned U.S. Pat. Nos. 6,198,531; 6,529,276; 7,123, 844; 7,834,999; 7,911,605; 7,920,258, 8,049,881, and U.S. patent application Ser. No. 12/094,460 (U.S. Pat. App. Pub. No. 2009/0219538); Ser. No. 12/094,465 (U.S. Pat. App. Pub. No. 2009/0219539); and Ser. No. 13/456,467, incorporated herein by reference, as indicated above.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to a characteristic of interest in the fluid 202, may be conveyed to a detector 212 for analysis and quantification. In some embodiments, the detector 212 is configured to produce an output signal in the form of a voltage that corresponds to the particular characteristic of interest of the fluid 202. In at least one embodiment, the signal produced by the detector 212 and the concentration of the characteristic of interest may be directly proportional. In other embodiments, the relationship may be a polynomial function, an exponential function, and/or a logarithmic function. The reflected optically interacted light 214, which may be related to characteristics of other components of the fluid 202, can be directed away from detector 212. In alternative configurations, the ICE 208 may be configured such that the reflected optically interacted light 214 can be related to the characteristic of interest, and the transmitted optically interacted light 210 can be related to other components or characteristics of the fluid 202.

In some embodiments, a second detector 216 can be present and arranged to detect the reflected optically interacted light 214. In other embodiments, the second detector 216 may be arranged to detect the electromagnetic radiation 204, 206 derived from the fluid 202 or electromagnetic radiation directed toward or before the fluid 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to one or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of interest being analyzed using the optical computing device 200 can be further processed computationally to provide additional characterization information about the fluid 202, or any reagents/products present therein. In some embodiments, the identification and concentration of each analyte of interest in the fluid 202 can be used to predict certain physical characteristics of the fluid 202. For example, the bulk characteristics of the fluid 202 can be estimated by using a combination of the properties conferred to the fluid 202 by each analyte.

In some embodiments, the concentration or magnitude of the characteristic of interest determined using the optical computing device 200 can be fed into an algorithm operating under computer control. The algorithm may be configured to make predictions on how the characteristics of the fluid 202 would change if the concentrations of the characteristic of interest are changed relative to one another. In some embodiments, the algorithm can produce an output that is readable by an operator who can manually take appropriate action, if needed, based upon the reported output. In other embodiments, however, the algorithm can take proactive process control by, for example, automatically adjusting the flow of a treatment reagent being introduced into a flow path or by halting the introduction of the treatment reagent in response to an out of range condition.

The algorithm can be part of an artificial neural network configured to use the concentration of each characteristic of interest in order to evaluate the overall characteristic(s) of the fluid 202 and predict how to modify the fluid 202 in order to alter its properties in a desired way. Illustrative but nonlimiting artificial neural networks are described in commonly owned U.S. patent application Ser. No. 11/986,763 (U.S. Patent App. Pub. No. 2009/0182693), which is incorporated herein by reference. It is to be recognized that an artificial neural network can be trained using samples of predetermined characteristics of interest, such as known reagents and products resulting from chemical processes involving such reagents, having known concentrations, compositions, and/or properties, and thereby generating a virtual library. As the virtual library available to the artificial neural network becomes larger, the neural network can become more capable of accurately predicting the characteristic of interest corresponding to a fluid, reagent, or product having any number of analytes present therein. Furthermore, with sufficient training, the artificial neural network can more accurately predict the characteristics of the fluid, even in the presence of unknown reagents and/or products.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a chemical reaction process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site (e.g., via wireless technology).

Figure 3:
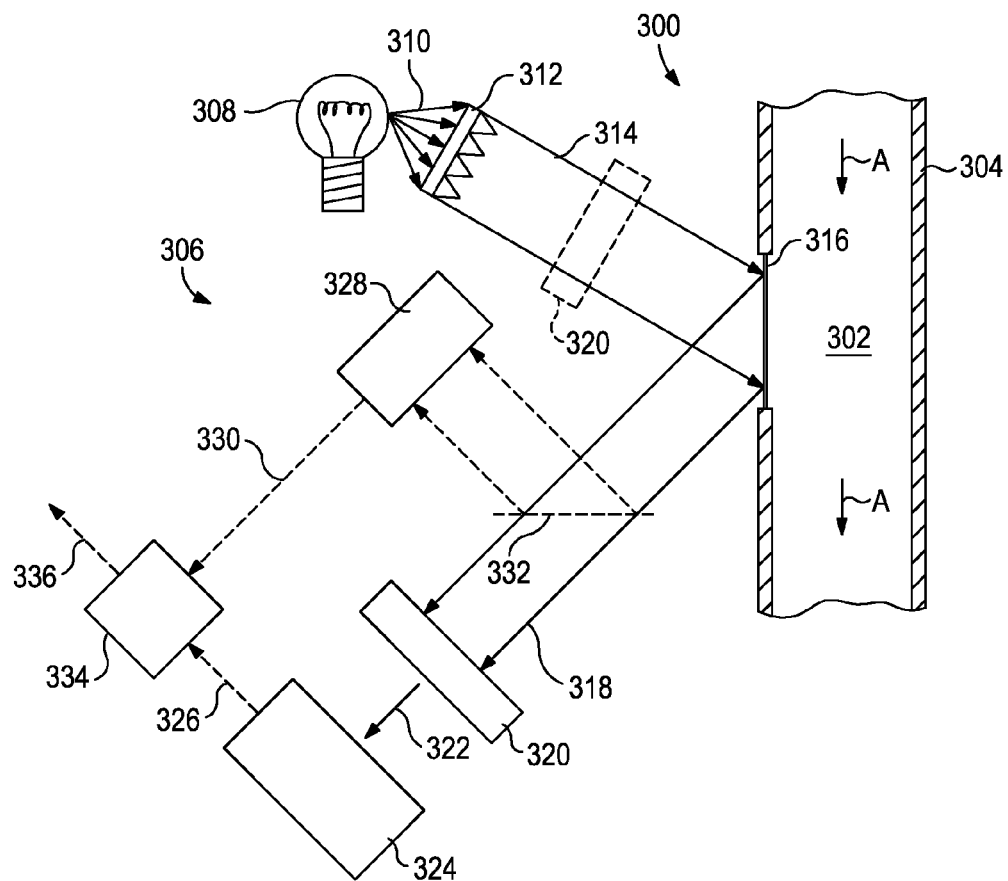
FIG. 3 illustrates an exemplary system for monitoring a fluid, according to one or more embodiments.

Referring now to FIG. 3, illustrated is an exemplary system 300 for monitoring a fluid 302, such as a chemical reaction process that may occur within the fluid 302, according to one or more embodiments. In the illustrated embodiment, the fluid 302 may be contained or otherwise flowing within an exemplary flow path 304. In at least one embodiment, the flow path 304 may be a flow line or a pipeline and the fluid 302 present therein may be flowing in the general direction indicated by the arrows A (i.e., from upstream to downstream). As will be appreciated, however, in other embodiments the flow path 304 may be any other type of flow path, as generally described or otherwise defined herein. For example, the flow path 304 may be a storage or reaction vessel and the fluid 302 may not necessarily be flowing while being monitored.

In at least one embodiment, however, the flow path 304 may form part of an oil/gas pipeline and may be part of a wellhead or a plurality of subsea and/or above-ground interconnecting flow lines or pipes that interconnect various subterranean hydrocarbon reservoirs with one or more receiving/gathering platforms or process facilities. In some embodiments, portions of the flow path 304 may be employed downhole and fluidly connect, for example, a formation and a wellhead. As such, portions of the flow path 304 may be arranged substantially vertical, substantially horizontal, or any directional configuration therebetween, without departing from the scope of the disclosure.

The system 300 may include at least one optical computing device 306, which may be similar in some respects to the optical computing device 200 of FIG. 2, and therefore may be best understood with reference thereto. While not shown, the optical computing device 306 may be housed within a casing or housing configured to substantially protect the internal components of the device 306 from damage or contamination from the external environment (e.g., the flow path 304). The housing may operate to mechanically couple the device 306 to the flow path 304 with, for example, mechanical fasteners, brazing or welding techniques, adhesives, magnets, combinations thereof or the like. In operation, the housing may be designed to withstand the pressures that may be experienced within or without the flow path 304 and thereby provide a fluid tight seal against external contamination. As described in greater detail below, the optical computing device 306 may be useful in determining a particular characteristic of the fluid 302 within the flow path 304, such as determining a concentration of a reagent present within the fluid 302, or a product resulting from a chemical process reaction occurring within the fluid 302. Knowing the concentration of reagents and/or products may help determine the overall quality of the fluid 302 and provide an opportunity to remedy potentially undesirable parameters of the fluid 302.

The device 306 may include an electromagnetic radiation source 308 configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, combinations thereof, or the like. In some embodiments, a lens 312 may be configured to collect or otherwise receive the electromagnetic radiation 310 and direct a beam 314 of electromagnetic radiation 310 toward the fluid 302. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the device 306 and the electromagnetic radiation 310 may instead be conveyed toward the fluid 302 directly from the electromagnetic radiation source 308.

In one or more embodiments, the device 306 may also include a sampling window 316 arranged adjacent to or otherwise in contact with the fluid 302 for detection purposes. The sampling window 316 may be made from a variety of transparent, rigid or semi-rigid materials that are configured to allow transmission of the electromagnetic radiation 310 therethrough. For example, the sampling window 316 may be made of, but is not limited to, glasses, plastics, semi-conductors, crystalline materials, polycrystalline materials, hot or cold-pressed powders, combinations thereof, or the like. In order to remove ghosting or other imaging issues resulting from reflectance on the sampling window 316, the system 300 may employ one or more internal reflectance elements (IRE), such as those described in co-owned U.S. Pat. No. 7,697,141, and/or one or more imaging systems, such as those described in co-owned U.S. patent application Ser. No. 13/456,467, the contents of each hereby being incorporated by reference.

After passing through the sampling window 316, the electromagnetic radiation 310 impinges upon and optically interacts with the fluid 302, including any reagents and/or chemical reaction products present within the fluid 302. As a result, optically interacted radiation 318 is generated by and reflected from the fluid 302. Those skilled in the art, however, will readily recognize that alternative variations of the device 306 may allow the optically interacted radiation 318 to be generated by being transmitted, scattered, diffracted, absorbed, emitted, or re-radiated by and/or from the fluid 302, or one or more reagents/products present within the fluid 302, without departing from the scope of the disclosure.

The optically interacted radiation 318 generated by the interaction with the fluid 302 may be directed to or otherwise received by an ICE 320 arranged within the device 306. The ICE 320 may be a spectral component substantially similar to the ICE 100 described above with reference to FIG. 1. Accordingly, in operation the ICE 320 may be configured to receive the optically interacted radiation 318 and produce modified electromagnetic radiation 322 corresponding to a particular characteristic of interest of the fluid 302. In particular, the modified electromagnetic radiation 322 is electromagnetic radiation that has optically interacted with the ICE 320, whereby an approximate mimicking of the regression vector corresponding to the characteristic of interest is obtained. In some embodiments, the characteristic of interest corresponds to the fluid 302. In other embodiments, the characteristic of interest corresponds to a particular reagent found in the fluid 302. In yet other embodiments, the characteristic of interest corresponds to a product resulting from a chemical reaction transpiring in the flow path 304.

It should be noted that, while FIG. 3 depicts the ICE 320 as receiving reflected electromagnetic radiation from the fluid 302, the ICE 320 may be arranged at any point along the optical train of the device 306, without departing from the scope of the disclosure. For example, in one or more embodiments, the ICE 320 (as shown in dashed) may be arranged within the optical train prior to the sampling window 316 and equally obtain substantially the same results. In other embodiments, the sampling window 316 may serve a dual purpose as both a transmission window and the ICE 320 (i.e., a spectral component). In yet other embodiments, the ICE 320 may generate the modified electromagnetic radiation 322 through reflection, instead of transmission therethrough.

Moreover, while only one ICE 320 is shown in the device 306, embodiments are contemplated herein which include the use of at least two ICE components in the device 306 configured to cooperatively determine the characteristic of interest in the fluid 302. For example, two or more ICE may be arranged in series or parallel within the device 306 and configured to receive the optically interacted radiation 318 and thereby enhance sensitivities and detector limits of the device 306. In other embodiments, two or more ICE may be arranged on a movable assembly, such as a rotating disc or an oscillating linear array, which moves such that the individual ICE components are able to be exposed to or otherwise optically interact with electromagnetic radiation for a distinct brief period of time. The two or more ICE components in any of these embodiments may be configured to be either associated or disassociated with the characteristic of interest in the fluid 302. In other embodiments, the two or more ICE may be configured to be positively or negatively correlated with the characteristic of interest. These optional embodiments employing two or more ICE components are further described in co-pending U.S. patent application Ser. Nos. 13/456,264, 13/456,405, 13/456,302, and 13/456,327, the contents of which are hereby incorporated by reference in their entireties.

In some embodiments, it may be desirable to monitor more than one characteristic of interest at a time using the device 306. In such embodiments, various configurations for multiple ICE components can be used, where each ICE component is configured to detect a particular and/or distinct characteristic of interest corresponding, for example, to the fluid 302, a reagent, or a product resulting from a chemical reaction in the fluid 302. In some embodiments, the characteristic of interest can be analyzed sequentially using multiple ICE components that are provided a single beam of electromagnetic radiation being reflected from or transmitted through the fluid 302. In some embodiments, as briefly mentioned above, multiple ICE components can be arranged on a rotating disc, where the individual ICE components are only exposed to the beam of electromagnetic radiation for a short time. Advantages of this approach can include the ability to analyze multiple characteristics of interest within the fluid 302 using a single optical computing device and the opportunity to assay additional characteristics simply by adding additional ICE components to the rotating disc corresponding to those additional characteristics.

In other embodiments, multiple optical computing devices can be placed at a single location along the flow path 304, where each optical computing device contains a unique ICE that is configured to detect a particular characteristic of interest. In such embodiments, a beam splitter can divert a portion of the electromagnetic radiation being reflected by, emitted from, or transmitted through the fluid 302 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 304. Likewise, multiple detection stations, each containing optical computing devices in parallel, can be placed in series for performing a similar analysis.

The modified electromagnetic radiation 322 generated by the ICE 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic of interest in the fluid 302. The voltage returned by the detector 324 is essentially the dot product of the optical interaction of the optically interacted radiation 318 with the respective ICE 320 as a function of the concentration of the characteristic of interest. As such, the output signal 326 produced by the detector 324 and the concentration of the characteristic of interest may be related, for example, directly proportional. In other embodiments, however, the relationship may correspond to a polynomial function, an exponential function, a logarithmic function, and/or a combination thereof.

In some embodiments, the device 306 may include a second detector 328, which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308. Undesirable radiating deviations can occur in the intensity of the electromagnetic radiation 310 due to a wide variety of reasons and potentially causing various negative effects on the output of the device 306. These negative effects can be particularly detrimental for measurements taken over a period of time. In some embodiments, radiating deviations can occur as a result of a build-up of film or material on the sampling window 316 which has the effect of reducing the amount and quality of light ultimately reaching the first detector 324. Without proper compensation, such radiating deviations could result in false readings and the output signal 326 would no longer be primarily or accurately related to the characteristic of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beamsplitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure.

In some applications, the output signal 326 and the compensating signal 330 may be conveyed to or otherwise received by a signal processor 334 communicably coupled to both the detectors 320, 328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328. In some embodiments, computationally combining the output and compensating signals 320, 328 may entail computing a ratio of the two signals 320, 328. For example, the concentration or magnitude of each characteristic of interest determined using the optical computing device 306 can be fed into an algorithm run by the signal processor 334. The algorithm may be configured to make predictions on how the characteristics of the fluid 302 change if the concentration of the measured characteristic of interest changes.

In real-time or near real-time, the signal processor 334 may be configured to provide a resulting output signal 336 corresponding to the characteristic of interest, such as a concentration of a reagent or resulting product present in the fluid 302. In some embodiments, as briefly discussed above, the resulting output signal 336 may be readable by an operator who can consider the results and make proper adjustments to the flow path 304 or take appropriate action, if needed, based upon the magnitude of the measured characteristic of interest. In some embodiments, the resulting signal output 328 may be conveyed, either wired or wirelessly, to the user for consideration.

In some embodiments, the resulting output signal 336 may be recognized by the signal processor 334 as being within or without a predetermined or preprogrammed range of suitable operation. For example, the signal processor 334 may be programmed with an impurity profile that corresponds to one or more known reagents that may be introduced into the flow path 304. The impurity profile may also correspond to one or more known products that result from a chemical reaction transpiring within the flow path 304. As such, the impurity profile may be a measurement of a concentration or percentage of one or more reagents/products within the flow path 304. In some embodiments, the impurity may be measured in the parts per million range, but in other embodiments, the impurity profile may be measured in the parts per billion or parts per thousand range and even in the percent range. If the resulting output signal 336 exceeds or otherwise falls within a predetermined or preprogrammed range of operation for the impurity profile, the signal processor 334 may be configured to alert the user (wired or wirelessly) of the same such that appropriate corrective action may be initiated, if needed. In some embodiments, however, the signal processor 334 may be configured to autonomously undertake the appropriate corrective action.

In one or more embodiments, the resulting output signal 336 may be indicative of a concentration of a reagent flowing with the fluid 302 and configured to react with, for example, another reagent or other substance found therein. In some embodiments, the reagent may be added to the flow path 304 to, for example, dissolve wax or asphaltene build-up, reduce a microbiological growth, etc. In other embodiments, the reagent may be a corrosion or scale inhibitor. In operation, the optical computing device 306 may be configured to determine and report the concentration of the reagent in near or real-time, thereby ascertaining whether the reagent is working properly. For example, the optical computing device 306 may be configured to determine when the reagent becomes fully saturated or reacted at some point, thereby indicating that the full potential of the reagent has been exhausted. In other embodiments, the optical computing device 306 may be configured to determine the concentration of unreacted reagents, thereby indicating the efficacy of an operation. This may prove advantageous in being able to more accurately determine the optimal amounts of treatment reagents to provide for a specific operation.

In other embodiments, the resulting output signal 336 may correspond to a product, or the concentration thereof, that results from a chemical reaction process between two or more reagents within the flow path 304. Exemplary products that may result from specific chemical reactions occurring within the flow path 304 include, but are not limited to, any organic, inorganic or enzymatic reaction products. In some embodiments, the characteristic of interest corresponding to the product may be indicative of, but not limited to, pH, viscosity, density or specific gravity, temperature, and ionic strength of a chemical compound. In yet other embodiments, the specific reagent(s) or product(s) detected or otherwise monitored by the optical computing device 306 may provide an indication as to the nature of a problem occurring within the flow path 304. For example, if a blockage or narrowing of the flow path 304 has occurred, monitoring the specific reagent(s) or product(s) may indicate whether such a blockage or narrowing was caused by asphaltenes, waxes, etc.

In some embodiments, the resulting output signal 336 may correspond to a near or real-time measurement of a chemical reaction process transpiring in the flow path 304, thereby allowing for the determination of reaction kinetics. For example, the optical computing device 306 may be configured to monitor the concentration of a reagent or product as a function of time. The main factors that may influence this reaction rate include the physical state of the reagents, the concentrations of the reagents, the temperature at which the reaction occurs, and whether or not any catalysts are present in the reaction. Methods of numerically determining reaction kinetics in real-time from experimentally derived spectrophotometric absorption data are well known to the skilled practitioner and are described within the article "Chemical Kinetics in Real Time: Using the Differential Rate Law and Discovering the Reaction Orders," *The Journal of Chemical Education*, Vol. 73 No. 7, July 1996, the contents of which are hereby incorporated by reference in their entirety.

Those skilled in the art will readily appreciate the various and numerous applications that the system 300, and alternative configurations thereof, may be suitably used with. For example, the system 300 may be employed to determine biocide efficacy and water treatment capabilities. In other applications, the system 300 may be used in conjunction with pollution control devices, such as scrubbers, or may be employed to monitor curing and degrees of cure of a substance such as, for example, cements in the oil and gas industry. In yet other embodiments, the system 300 may be used to monitor aging of a material, or other environmentally induced reaction(s)/process(es). For instance, the system 300 may be configured to monitor degradation on one or more polymers, such as those found on hoses, o-rings, etc. The system 300 may also be configured to monitor degradation of biologic materials such as, but not limited to, masonry materials (e.g., stone, brick, cement, etc.), glass, metals (i.e., corrosion), fluids, combinations thereof, and/or the like. As will be appreciated, such degradation may result from at least UV-light, sunlight, and temperature in addition to the various chemical aging substances and agents (e.g., acids, etc.). Accordingly, the system 300 may be useful in monitoring the general condition of flexible risers, hoses, rig foundations, rust on pipes, inner and outer coatings, and the like.

Figure 4:
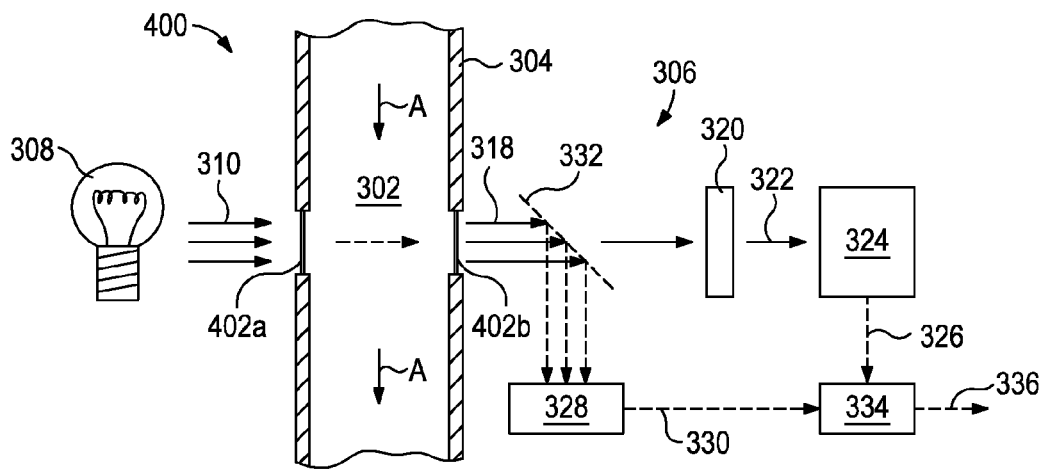
FIG. 4 illustrates another exemplary system for monitoring a fluid, according to one or more embodiments.

Referring now to FIG. 4, illustrated is another exemplary system 400 for monitoring a fluid 302, such as a chemical reaction process that may occur within the fluid 302, according to one or more embodiments. The system 400 may be similar in some respects to the system 300 of FIG. 3, and therefore may be best understood with reference thereto where like numerals indicate like elements that will not be described again. As illustrated, the optical computing device 306 may again be configured to determine a characteristic of interest of the fluid 302 as contained within the flow path 304. Unlike the system 300 of FIG. 3, however, the optical computing device 306 in FIG. 4 may be configured to transmit the electromagnetic radiation through the fluid 302 via a first sampling window 402a and a second sampling window 402b arranged radially-opposite the first sampling window 402a. The first and second sampling windows 402a,b may be similar to the sampling window 316 described above in FIG. 3.

As the electromagnetic radiation 310 passes through the fluid 302 via the first and second sampling windows 402a,b, it optically interacts with the fluid 302, and potentially with at least one reagent and/or product present therein. Optically interacted radiation 318 is subsequently directed to or otherwise received by the ICE 320 as arranged within the device 306. It is again noted that, while FIG. 4 depicts the ICE 320 as receiving the optically interacted radiation 318 as transmitted through the sampling windows 402a,b, the ICE 320 may equally be arranged at any point along the optical train of the device 306, without departing from the scope of the disclosure. For example, in one or more embodiments, the ICE 320 may be arranged within the optical train prior to the first sampling window 402a and equally obtain substantially the same results. In other embodiments, one or each of the first or second sampling windows 402a,b may serve a dual purpose as both a transmission window and the ICE 320 (i.e., a spectral component). In yet other embodiments, the ICE 320 may generate the modified electromagnetic radiation 322 through reflection, instead of transmission therethrough. Moreover, as with the system 300 of FIG. 3, embodiments are contemplated herein which include the use of at least two ICE components in the device 306 configured to cooperatively determine the characteristic of interest in the fluid 302.

The modified electromagnetic radiation 322 generated by the ICE 320 is subsequently conveyed to the detector 324 for quantification of the signal and generation of the output signal 326 which corresponds to the particular characteristic of interest in the fluid 302. As with the system 300 of FIG. 3, the system 400 may also include the second detector 328 for detecting radiating deviations stemming from the electromagnetic radiation source 308. As illustrated, the second detector 328 may be configured to receive a portion of the optically interacted radiation 318 via the beamsplitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure. The output signal 326 and the compensating signal 330 may then be conveyed to or otherwise received by the signal processor 334 which may computationally combine the two signals 330, 326 and provide in real-time or near real-time the resulting output signal 336 corresponding to the concentration of the characteristic of interest in the fluid 302.

Still referring to FIG. 4, with additional reference to FIG. 3, those skilled in the art will readily recognize that, in one or more embodiments, electromagnetic radiation may be derived from the fluid 302 itself, and otherwise derived independent of the electromagnetic radiation source 308. For example, various substances naturally radiate electromagnetic radiation that is able to optically interact with the ICE 320. In some embodiments, for example, the fluid 302, or the reagent or product present within the fluid 302, may be a blackbody radiating substance configured to radiate heat that may optically interact with the ICE 320. In other embodiments, the fluid 302, or the reagent or product within the fluid 302, may be radioactive or chemo-luminescent and, therefore, radiate electromagnetic radiation that is able to optically interact with the ICE 320. In yet other embodiments, the electromagnetic radiation may be induced from the fluid 302, or the reagent or product within the fluid 302, by being acted upon mechanically, magnetically, electrically, combinations thereof, or the like. For instance, in at least one embodiment, a voltage may be placed across the fluid 302, or the reagent or product within the fluid 302, in order to induce the electromagnetic radiation. As a result, embodiments are contemplated herein where the electromagnetic radiation source 308 is omitted from the optical computing device 306.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method of monitoring a fluid, comprising:
containing the fluid in which a chemical reaction is occurring within a flow path;
interacting an electromagnetic radiation source with the fluid to form a sample interacted light;
separating a portion of the sample interacted light with a beam splitter;
measuring the intensity of the separated portion of the sample interacted light with a first detector to form a compensating signal indicative of radiative deviations from the electromagnetic radiation source;
optically interacting at least one integrated computational element with the fluid using the sample interacted light, thereby generating modified electromagnetic radiation, the integrated computational element comprising a plurality of layers of dielectric materials deposited on an optical substrate according to a characteristic of the chemical reaction;
producing an output signal by measuring the modified electromagnetic radiation with a second detector coupled to the integrated computational element;
receiving the output signal and the compensating signal with a signal processor communicably coupled to the first and second detectors; and
determining the characteristic of the chemical reaction with the signal processor by comparing the output signal with the compensating signal,
wherein the processor is programmed to adjust a flow of a treatment reagent being introduced into a flow path based on the determined characteristic of the chemical reaction in response to an out of range condition.

2. The method of claim 1, wherein interacting an electromagnetic radiation source with the fluid comprises at least one of reflecting a light generated by the electromagnetic radiation source from a window in contact with the fluid, and transmitting the light generated by the electromagnetic radiation source through the fluid.

3. The method of claim 2, further comprising reflecting the electromagnetic radiation off the fluid or transmitting the electromagnetic radiation through the fluid.

4. The method of claim 1, wherein the first detector and the second detector are different detectors.

5. The method of claim 1, wherein comparing the output signal with the compensating signal comprises computing a ratio of the output signal to the compensating signal.

6. The method of claim 1, wherein the characteristic of the chemical reaction comprises a concentration of one or more reagents in the fluid.

7. The method of claim 6, wherein the one or more reagents in the fluid comprises at least one selected from the group consisting of barium, calcium, manganese, sulfur, iron, strontium, chlorine, paraffins, waxes, asphaltenes, aromatics, saturates, foams, salts, particulates, sand, and any combinations thereof.

8. The method of claim 6, wherein the one or more reagents in the fluid comprises at least one substance selected from the group consisting of acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, particulate diverters, salts, fluid loss control additives, gases, catalysts, clay control agents, chelating agents, corrosion inhibitors, dispersants, flocculants, scavengers, lubricants, breakers, delayed release breakers, friction reducers, bridging agents, viscosifiers, weighting agents, solubilizers, rheology control agents, viscosity modifiers, pH control agents, hydrate inhibitors, relative permeability modifiers, diverting agents, consolidating agents, fibrous materials, bactericides, tracers, probes, nanoparticles, tetrakis hydroxymethyl phosphonium sulfate (THPS), glutaraldehyde, benzalkonium chloride, algal/fungal/bacterial deposits, imidazoline derivatives, quaternary ammonium salts, alkaline zinc carbonate, amines, any derivatives thereof, and any combinations thereof.

9. The method of claim 1, wherein the characteristic of the chemical reaction comprises a concentration of a product resulting from the chemical reaction.

10. The method of claim 1, wherein the characteristic of the chemical reaction comprises a characteristic selected from the group consisting of a chemical composition, an impurity content, a pH level, a temperature, a viscosity, a density, an ionic strength, a total dissolved solids measurement, a salt content measurement, a porosity, an opacity measurement, a bacteria content, and any combinations thereof.

* * * * *